United States Patent [19]
Del Mar et al.

[11] Patent Number: 5,205,295
[45] Date of Patent: Apr. 27, 1993

[54] METHOD AND APPARATUS FOR HOLTER RECORDER WITH HIGH RESOLUTION SIGNAL AVERAGING CAPABILITY FOR LATE POTENTIAL ANALYSIS

[75] Inventors: Bruce Del Mar, Laguna Beach; Isaac R. Cherry, Mission Viejo, both of Calif.

[73] Assignee: Del Mar Avionics, Irvine, Calif.

[21] Appl. No.: 932,907

[22] Filed: Aug. 18, 1992

Related U.S. Application Data

[63] Continuation-in-part of Ser. No. 710,377, Jun. 3, 1991, abandoned.

[51] Int. Cl.$^5$ .......................................... A61B 5/0436
[52] U.S. Cl. ................................................. 128/711
[58] Field of Search ........................ 128/696, 710, 711

[56] References Cited

U.S. PATENT DOCUMENTS

| | | | |
|---|---|---|---|
| 4,006,737 | 2/1977 | Cherry | 128/711 |
| 4,457,315 | 7/1984 | Bennish | 128/711 |
| 4,475,558 | 10/1984 | Brock | 128/710 |
| 4,712,560 | 12/1987 | Schaefer | 128/696 |
| 5,002,062 | 3/1991 | Suzuki | 128/710 |
| 5,086,778 | 2/1992 | Mueller et al. | 128/710 |

*Primary Examiner*—William E. Kamm
*Attorney, Agent, or Firm*—James D. Leimbach

[57] ABSTRACT

A method and apparatus for an ambulatory electrocardiographic monitoring system for recording, detection, measurement, analysis and plotting of high resolution electrocardiographic data having a modified Holter recorder that performs digital signal averaging of selected signals as well as storing for future playback all ECG beats. The digitally signal averaged beats are correlated with a previously defined correlation coefficient yielding summated results that have eliminated nonrepetitive noise to less than a microvolt. By real time averaging approximately 1000 beats during a 10 to 15 minute period and digitally storing the averaged data, micropotential averaging can be performed several times per hour for up to 24-hours. Analog recordings are precalibrated for accurate amplitude representation as well as providing an option for standard one millivolt calibration pulses at the beginning of the tape. Digital recordings are precalibrated relative to the acceptable levels without the use of a calibration signal. The recordings are downloaded to analysis systems at high speeds. If the recordings are analog they are digitized at a sufficiently high enough resolution to permit analysis of micropotentials. All recorded data is transferred to computer memory and hard disk for further review by the analysis system.

27 Claims, 10 Drawing Sheets

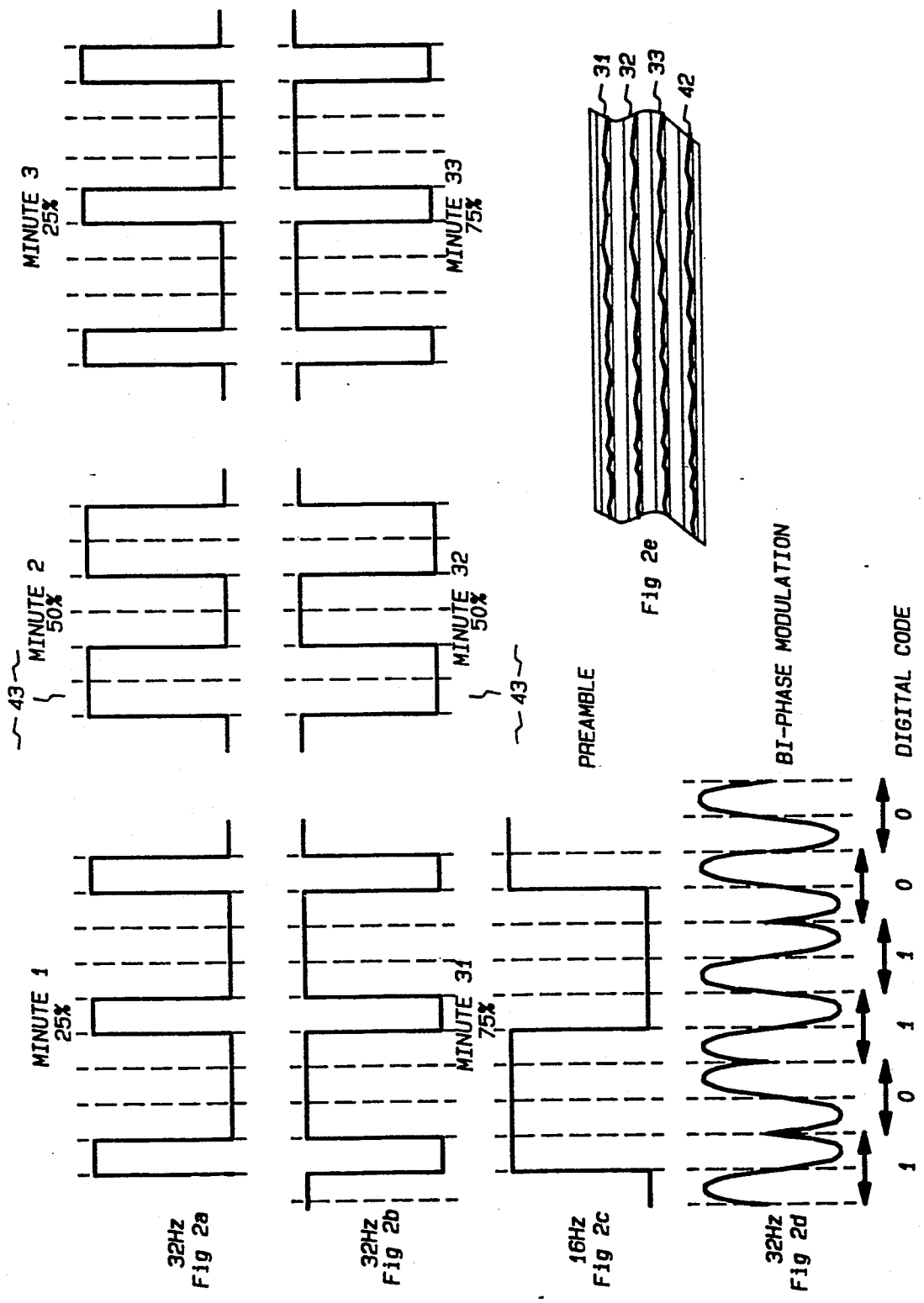

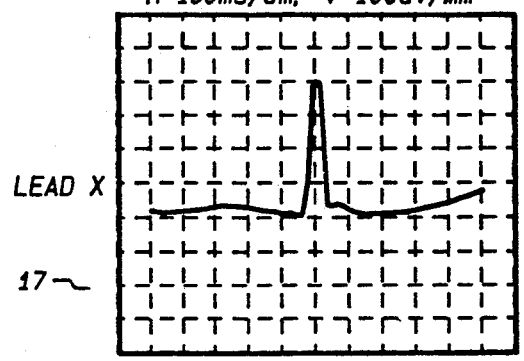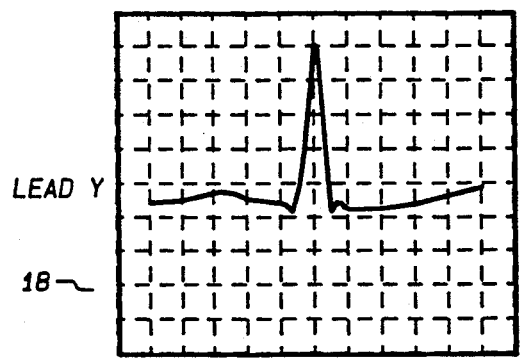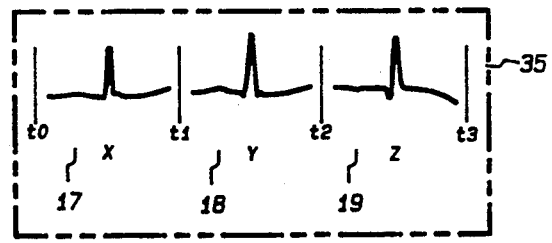
FIGURE 3b
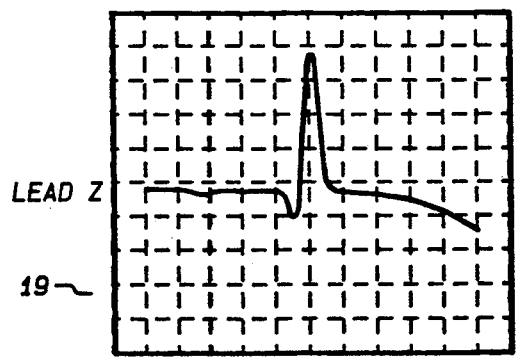
FIGURE 3a

METHOD AND APPARATUS FOR HOLTER RECORDER WITH HIGH RESOLUTION SIGNAL AVERAGING CAPABILITY FOR LATE POTENTIAL ANALYSIS

This is a continuation-in-part of co-pending application Ser. No. 07/710,377 filed on Jun. 3, 1991 now abandoned.

BACKGROUND OF THE INVENTION

1. Field of the Invention

This invention relates generally to the field of electrocardiographic (ECG) recording of very low amplitude micropotential signals known as late potentials, and more emphatically, the teachings of this invention extend Holter applications to performing a real time analysis of late potentials while simultaneously storing, within the same Holter recording medium, multiple channels of ECG data for a standard 24 hours, or more. Late potential assessment time periods are selected during which the multiple channel ECG is sampled for the presence of late potentials. A high resolution digital average of multiple channel ECG data is stored in a Holter recording medium of analog tape, digital tape, solid state memory, rotating magnetic disc, rotating optical disc, rotating magneto-optical memory, removable memory card storage using either solid state or optical technologies, or any sequential or random storage system. This storage system will store high resolution digital data for later presentation and analysis on an ECG scanning computer. The high resolution data stored is useful in the analysis of micropotentials and specifically in determining the existence of ventricular late potentials which are evidence of ventricular tachycardia.

2. Description of the Related Art

Due to size and weight restrictions, conventional Holter recorders presently available in the medical profession employ lightweight battery-powered recorders having magnetic tape or solid-state memory for storage. The conventional recorders employing magnetic tape storage, normally store ECG recordings up to 24-hours, or more, of multiple channel ECG data. The recorded ECG data can then be played back at many times the recording speed, to generate post-recording reports. The ECG data stored on these magnetic tape based Holter recorders is typically stored in an analog format from 0.1 Hz to 100 Hz, whereas, frequencies from 10 to 250 Hz are required to perform micropotential analysis of late potentials. Conventional solid-state Holter recorders have the capability to record at of 1000 samples per second or more with between 8 to 12 bits of digital resolution which is equivalent to magnetic tape based recorders of D.C. to 300 Hz with an accurate amplitude resolution of 0.4% or better without employing calibration signals. In an effort to reduce the memory requirements of an ambulatory system, solid state Holter recorders normally employ data compaction algorithms. Numerous data compaction algorithms are available, and all result in at least a partial loss of the original data. It is well known in the art of electrocardiography that conventional Holter recorders receive signal inputs that have background noise in the range of 20 to 50 microvolts. Thus, thresholding techniques must strip away the lower 50 microvolts of a signal in attempts to reduce the noise that is inherent with the input. As a result of these limitations, conventional Holter monitoring is concentrated with signals in the range of a millivolt. The ability of these solid state recorders to record micropotentials is, therefore, subject to limitations due to size, weight, power and memory capacity to record a full 24 hours of late potential data.

The analysis of micropotentials concerns the analysis of signals in the microvolt range and requires sensitivity not attainable with conventional Holter techniques. Conventional Holter recording permits substantially higher noise levels (20 to 50 microvolts) than the signal to be measured in micropotential analyzing. One of the solutions to the problem of extraneous noise has been the use of digital signal averaging techniques, wherein, averaging is accomplished over a time period of five or ten minutes, during which time it is preferable that patient activity be at a minimum to avoid artifact. The signal averaging techniques employed by ECG analysis systems known to the art, allow the analysis of signals on the order of a microvolt by relying on the basic principle that the repetitive nature of a bioelectric signal allows the signal to be averaged over a sufficiently large number of samples. During this averaging process, nonrepetitive noise will be effectively eliminated by the signal averaging process, due to the nonrepetitive nature of the noise. The larger the number of samples that are averaged, the more effective the signal averaging techniques are at eliminating noise. By digitizing the electrocardiographic signals and converting the signals into a series of corresponding points, computational methods can then be employed to average the corresponding points of the sampled electrocardiographic signals. The results yielded are necessarily related to the resolution used in digitizing. Noise or artifact that is nonrepetitive is thereby reduced or eliminated, for all practical purposes, by signal averaging a sufficiently large sample of input signals. Thus, repetitive signals can be effectively signal averaged to eliminate noise that is of a nonrepetitive nature.

Holter techniques have also been disclosed in which the resulting recording was itself analyzed for the presence of micropotentials without the use of additional equipment. Such a system is taught by U.S. Pat. No. 4,883,065 issued to Kelen, and assigned to the assignee of the present invention, wherein conventional Holter recordings were used in the analysis of micropotentials. These conventional recordings store and record up to 24-hours of three channels of ECG data. The stored ECG data can then be used to generate post recording reports. However, the fidelity of the signals recorded on these conventional systems is lacking due to the high frequency limitation in the vicinity of 50 to 100 Hz found in most Holter systems.

As can be seen by the foregoing discussion, the disclosure of the prior art lacks in the teachings relating to micropotential analysis on an 24 hour ambulatory basis. Digital systems with sampling rates of 1000 samples per second and 12 bit digital accuracy are required for sufficient fidelity to perform micropotential analysis. Systems that can sample such high rates in real time require large amounts of memory to hold 24 hours of data, typically 500 megabytes. Currently available signal averaging systems, used in micropotential analyzing, require the patient to be wired to the system while at rest for short 5-10 minute epochs. These systems will signal average the short periods in real time and display the results but require large hard disks if all the 24 hours of data is to be stored. Therefore, there remains a need within the art for a method and apparatus capable of performing a continuous, high resolution, real time analysis of ECG late potentials that can be stored on the type of storage medium used with a Holter recording device. This is provided by the teachings of the present invention wherein a recording of a digitized average of a multiple channel ECG is used to identify and store late potentials during selected time epochs and continuously over periods of 24 hours or more.

SUMMARY OF THE INVENTION

We have discovered that specific micropotentials, classified as late potentials, can be stored on Holter (long-term ambulatory) recording devices, either continuously or during multiple sampling periods. Specifically, high frequency electrocardiographic signals can be recorded on multiple channel Holter devices by creating a high resolution digital equivalent for each of the multiple channels and employing signal averaging techniques to reduce the associated signal noise to less than one microvolt. Disclosed by the invention is a method and apparatus to store continuous or multiple episodes of micropotentials for periods up to 24-hours or for multiple day periods. A summation of signal averages for each of the multiple channels to an ECG complex is created and then stored on one of the multiple channels, or within a storage medium, on a periodic basis. The recording of a summation of signal averages is done in real time with the recording of ECG data. Thus, each heartbeat for the entire period can be recorded in any of the disclosed formats, analog tape, digital tape, solid-state digital, compressed solid-state digital format, rotating magnetic memory, rotating optical memory, rotating magneto-optical memory, memory card storage made from either solid state or optical technology, or any other sequential or random access storage device. Furthermore, a high resolution digital representation of the ECG's is used to create the summated average, which summated average may then be recorded using any of the disclosed storage mediums.

It is the object of this invention to record on an ambulatory basis multiple channels of electrocardiographic signals from a single set of electrodes while simultaneously recording a digital signal average of all beats within selected segments that have been correlated to a previously defined correlation coefficient, thus eliminating extraneous nonreptitive noise components, and to store these recordings on the same storage medium.

It is further the object of this invention to provide a method of recording a digital signal average of selected beats on the same recording medium used to store all beats received from a single set of electrodes, such that the method can be employed on either: analog tape; digital ambulatory tape; solid state memory; rotating memory including magnetic, optical or magneto-optical; memory card mass storage devices in either solid state or optical; or any sequential or random access memory capable of storing and recording data for future playback and analysis.

It is further the object of this invention to provide an ambulatory means of digital signal averaging electrocardiographic signals in which there is a digital accuracy of 12 bits or more in order to provide the capability of averaging out nonrepetitive noise components on the order of a microvolt.

It is further the object of this invention to provide a system in which a continuous stream of data consisting of signal averaged beats and ECG data, recorded over the entire time period, can be played back in an ECG analysis system and placed into a digital format to be stored in memory, either magnetic, optical or magneto optical disc storage or memory cards with disk storage in a computer.

It is further the object of this invention to create a method of recording, on the same storage medium, both a total record of ECG beats and a digital signal average of selected beats in which the digitally signal averaged beats can be recorded on a separate recording channel or on one of the ECG recording channels.

BRIEF DESCRIPTION OF THE DRAWINGS

FIG. 2a is a series of waveforms illustrating the timing signal used to storage beat averaged data during the first half of every hour.

FIG. 2b is a series of waveforms illustrating the timing signal used to store beat averaged data during the second half of every hour.

FIG. 2c shows the preamble that proceeds the transmission of modulated data.

FIG. 2d is an illustration of the bi-phase modulation used to store data on tape.

FIG. 2e is a diagram of the magnetic tape showing four separate tracks on which data can be stored.

FIG. 3a shows the three typical summated signal averaged beats.

FIG. 3b is an illustration of the sequential output of the three summated signal averaged beats.

DESCRIPTION OF THE PREFERRED EMBODIMENT

The following description is intended to enable any person skilled in the arts of Holter monitoring or electrocardiographic analysis systems to make and use the present invention as disclosed herein, and details the best modes known to the inventor of making and using the invention. Various alterations to the concepts disclosed in the present invention will be obvious to those skilled in the above referenced arts, it is therefore, possible that the invention be practiced by means other than those specifically disclosed herein.

The present invention discloses a method and apparatus for performing a realtime analysis of electrocardiographic signals on an ambulatory basis (Holter), and although the present invention may have alternate data processing uses, Holter monitoring is the area of concentration for this embodiment.

Figure 1:
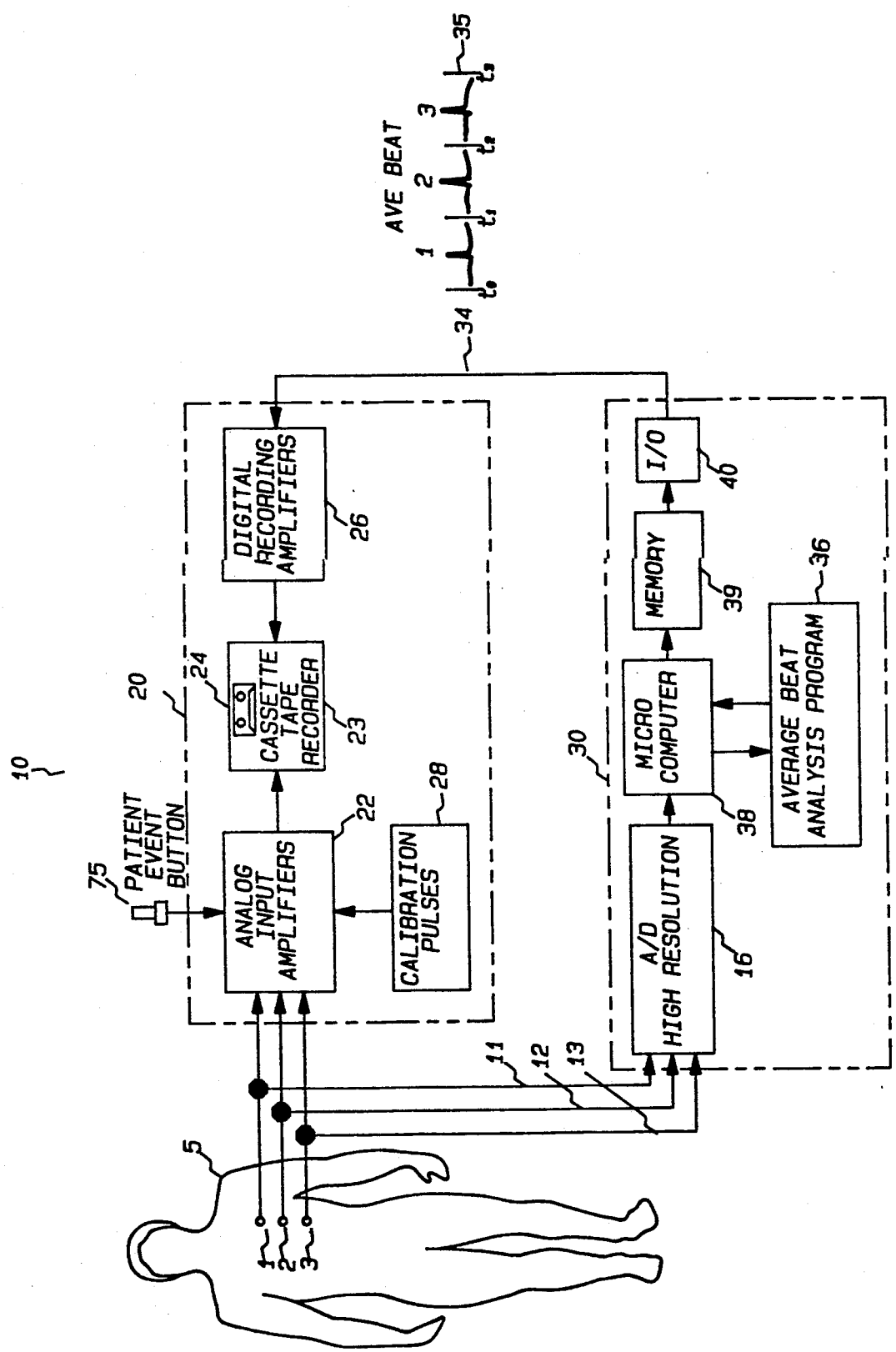
FIG. 1 is a block diagram for the recording portion of the present invention employing cassette tape as a storage medium.

Referring to FIG. 1, which details a block diagram for the present invention employing magnetic cassette tape as a storage medium, high resolution recorder, generally referred to as 10, is connected to patient 5 by three electrocardiographic (ECG) sensor electrodes 1, 2, 3. The ECG sensor electrodes 1, 2, 3 are analog sensing devices capable of detecting the bioelectric signals of the heart. Sensor electrodes 1, 2, 3 are physically connected to high resolution recorder 10 and electrically connected to each the storage unit 20 and the signal averaging unit 30. The storage unit 20 is a modified version of Holter recorders well known to the art, having analog input amplifiers 22 operative to increase the amplitude of the analog signals received, by ECG channels 11, 12, 13, from sensor inputs 1, 2, 3 to a level sufficient for recording these signals on cassette tape 24. Calibration pulses 28 are generated in the preferred embodiment of the present invention to assist the analog input amplifiers 22 in providing proper amplification for signals on ECG channels 11, 12, 13. However, it is not an essential ingredient of the invention to use calibration pulses. A novel feature of storage unit 20 is the capability to receive and store the beats that have been digitally signal averaged by the signal averaging unit 30.

The signal averaging unit 30 receives digital versions of the ECG channels 11, 12, 13 from the high resolution A/D convertors 16 which performs an analog to digital conversion with 12 bit accuracy. These digital signals are used to identify and analyze late potentials by the microcomputer 38 and as data for the beat averaging analysis 36 program. The beat averaging program 36 will perform a simultaneous digital average of all the desired beats. In the preferred embodiment of the invention 1000 beats will typically be averaged. The averaged beats will then be correlated with a previously defined correlation coefficient, typically 0.98, thus eliminating extraneous nonrepetitive noise components and other irregular ECG beats. By performing the beat averaging analysis with a 12 bit digital word, the averaged beat can be resolved down to one microvolt or less with a signal to noise ratio of one. Once microcomputer 38 has performs beat averaging analysis program 36 on the desired data, microcomputer 38 stores the averaged beat data into memory 39 where it will be held prior to being output by the I/O Section 40 to the storage unit 20.

Referring to FIG. 2 and FIG. 3 in conjunction with FIG. 1, averaged beats 35 are serially transmitted 34 from the signal averaging unit 30 to the storage unit 20 and stored serially in a digital format on timing track 42 of analog magnetic cassette tape 24 as digital signals at a typical frequency of 32 Hz. Consequently, the rate at which these signals can be stored limits the minimum time epoch, for signal averaging purposes, due to the fact that timing track 42 on analog magnetic cassette tape 24 (which has a typical maximum data storage rate of 32 Hz due to tape bandwidth limitations) is being used as a storage medium. Averaged beats 35 will be stored as summated signal averages, of selected time epochs, for each of the ECG channels being recorded. Thus, in the preferred embodiment, there will be three summated signal averages stored every sampling period, one per each ECG channel 11, 12, 13 . A sampling period is typically 10 to 15 minutes long, in this manner approximately 1000 beats or more can be signal averaged. The digital recording amplifiers 26 operate to properly interface the storage unit 20 with the micropotential analysis results that are received from the signal averaging unit 30.

Referring to FIG. 3a, and FIG. 3b shows are three typical summated signal averaged beats 17, 18, 19 for ECG channels 11, 12, 13 as used in the present invention. The summated signal averaged beats 17,18, 19 are calculated using conventional signal averaging techniques. These beats are typically averaged over 500 ms periods by microcomputer 38. Upon completion of the averaging process, the summated signal averaged beats 17, 18, 19 are placed into memory 39 where they will be sequentially output as a digital signals by I/O 40 during respective time periods, $t_0$ to $t_1$, $t_1$ to $t_2$, and $t_2$ to $t_3$ as a serial bit stream 34 of data representative of averaged beats 35 typically at a 32 Hz frequency.

As shown in FIG. 1 seen in conjunction with FIG. 2a through FIG. 2e, the embodiment of the invention using magnetic tape as a storage medium, signal averaging unit 30 outputs serial bit stream 34 of data containing averaged beat data 35 through IO section 40 to be recorded on standard timing track 42 on cassette 24 of recorder 23. Standard timing signals 43 on timing track 42 are recorded at a typical frequency of 32 Hz on a forth channel on recorder 23. As can be seen in FIG. 2a, and FIG. 2e the timing signal 43 is a modulated signal with a duty cycle which alternates between succeeding minutes and again between half hour segments. Here, during the first half of every hour, the timing signal 43 used during odd numbered minutes, i.e minutes 1, 3, 5 etc. will have a 25% duty cycle, while the timing signal 43 used during the even numbered minutes, 2, 4, 6 etc. will have a 50% duty cycle, as shown in FIG. 2a. During the second half of every hour, the odd numbered minutes will have a 75% duty cycle while the even numbered minutes will have a 50% duty cycle, as shown in FIG. 2b. The entire process then repeats itself after the end of one hour. Modulation of the timing track during the digital data insertion can use different methods, the preferred embodiment uses bi-phase modulation techniques such as bi-phase mark, seen in FIG. 2d, in which negative portions of the sine wave are interpreted as binary O's and positive portions of the sine wave are interpreted as binary ones. A distinctive preamble, shown in FIG. 2c, at 16 Hz is also inserted into the data stream prior to the data byte block to identify the start of the exact data byte data block. FIG. 2c shows the preamble which is sent on the timing signal 43 for a 30 second period, prior the transmission of modulated data. After the preamble, the digital data is modulated onto the timing track with error correction and redundancy for a typical period of 12.5 minutes. At the end of this period, the timing track returns to normal, updating the playback system on a minute by minute basis, as discussed above, until any successive average beat epoch again interrupts the conventional operation of the timing channel. The above manner of maintaining the typical timing frequency ar 32 Hz allows the simultaneous transmission of digital data modulated with timing signals on a playback system employing a speed control system for the magnetic tape that is a servo mechanism.

The A/D convertors 16 provide digital data for the average beat analysis program 36 at a sample rate of 1000 samples per second. Each sample is represented by two digital bytes (16 bits). Desired sampling around the "R" wave of an electrocardiographic signal, as seen in FIG. 3., takes 500 mSec, during which time 500 samples will be taken each requiring 16 bits to represent or 8000 bits. Although, two bytes are used to represent each sample, only 12 bits are true data, these 12 bits reflecting the 12 bit accuracy of the A/D convertors 16. The four most significant bits (MSB's) are duplicates of the second four MSB's and are used only for error correction. Since there are three ECG channels to average, a total of 24000 bits must be stored for each epoch. Average beat 36 will average all data received for each epoch over a 10-15 minute period. The final summated average for all three channels during the 10-15 minute period will also require 24,000 bits to represent. These 24000 bits are the summated signal average beats 17, 18, 19 that represent the three ECG channels 11, 12, 13 digitally signal averaged over the desired time period. Serial bit stream 34 containing averaged beats 35 is transmitted to storage unit 20 and recorded on cassette tape 24 at a rate of 32 Hz, this recording takes 750 seconds of tape time equal to 12.5 minutes. This time period being equal to the minimum time epoch.

Standard compression techniques can reduce the size of the 24,000 bits representative of summated signal averaged beats 17, 18, 19 in order to achieve shorter time epochs. Error typical correction algorithms can be employed to insert error correction bits used into bit stream 34 via CPU 37 and analysis program 36. The algorithm is then later decoded in the playback system where data is corrected in cases of loss due to tape dropout characteristics.

Data from the signal averaging unit 30 will be used by the storage unit 20 to be stored on one of the channels on the cassette tape 24. Basically two methods can be used to accomplish this. The first method, that discussed above, is to have four independent channels on the cassette 24 on which to store data. As shown in FIG. 2e, there are three ECG channels 17, 18, 19 used to store analog ECG data from the sensor electrodes and a single timing track 42. On this timing track 42 digital signal averaged data would be stored as discussed above. Another possible method is to interrupt one of the three channels used to store ECG data and on that interrupted channel store the signal averaged version in a digital format. This method would, however, entail a loss of ECG data for that interrupted channel.

Figure 4:
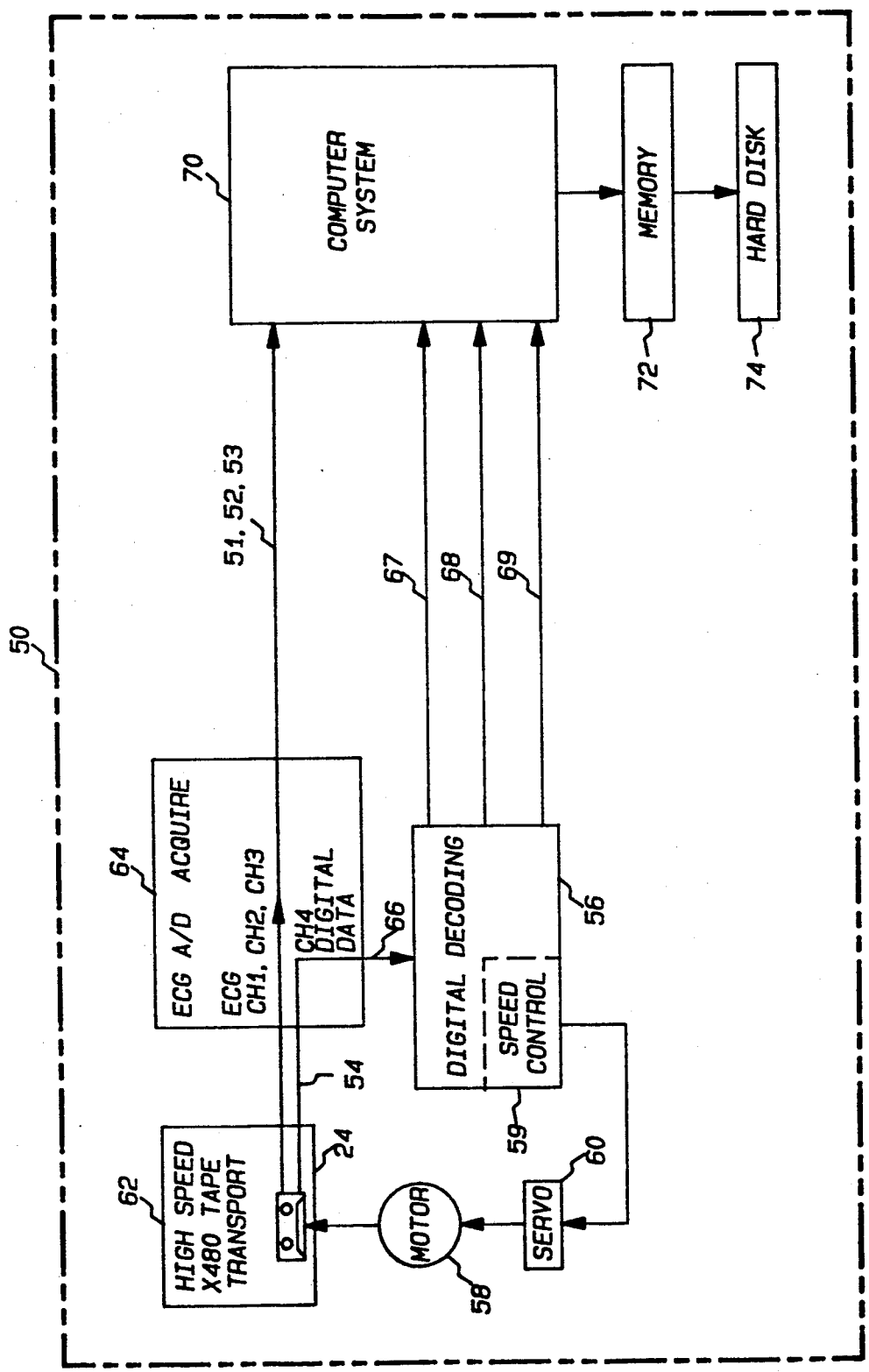
FIG. 4 is a block diagram representation of the playback system as disclosed by the present invention.

The recording, made using magnetic tape as the storage medium, can be played back for analysis using the playback system as seen in FIG. 4. The playback system, generally referred to as 50, is a modified version of conventional Holter tape scanners. Well known are the ECG A/D Acquire features 64 which receive the analog ECG data from the cassette tape 24 and convert the analog data to digital, the digital version for the three ECG channels 51, 52, 53 are then sent to the computer system 70 within the scanner 50. The acquire features used in ECG analysis which are also well known to the art. However, a novel feature is the digital decoding interface 56 that interfaces the high speed tape transport 62 to the computer system 70. In this manner the signal averaged beat data 66 is taken from cassette tape 24 from either a totally independent channel 54 as in the preferred embodiment or possibly as one of the ECG channels, and decoded by the Digital Decoding Interface 56 to generate patient event 67, timing signals 68, and the signal averaged beats 69. This data may then be used by the computer system 70 of the Scanner 50. Therefore, the computer system 70 scanner 50 is immediately supplied with an analysis of micropotentials in terms of the summated signal average. The computer 70 will perform further ECG analysis on received data and place the data into memory 72 and finally into hard disk 74 storage. In the preferred embodiment, motor 58 is controlled by servo 60 which is in turn controlled by speed control 59 of the digital decoding. As stated previously, simultaneous transmission of digital data modulated with timing signals can be accomplished on a playback system by having a motor 58 with a speed controlled 59 servo mechanism 60 used to drive tape 25.

Figure 5:
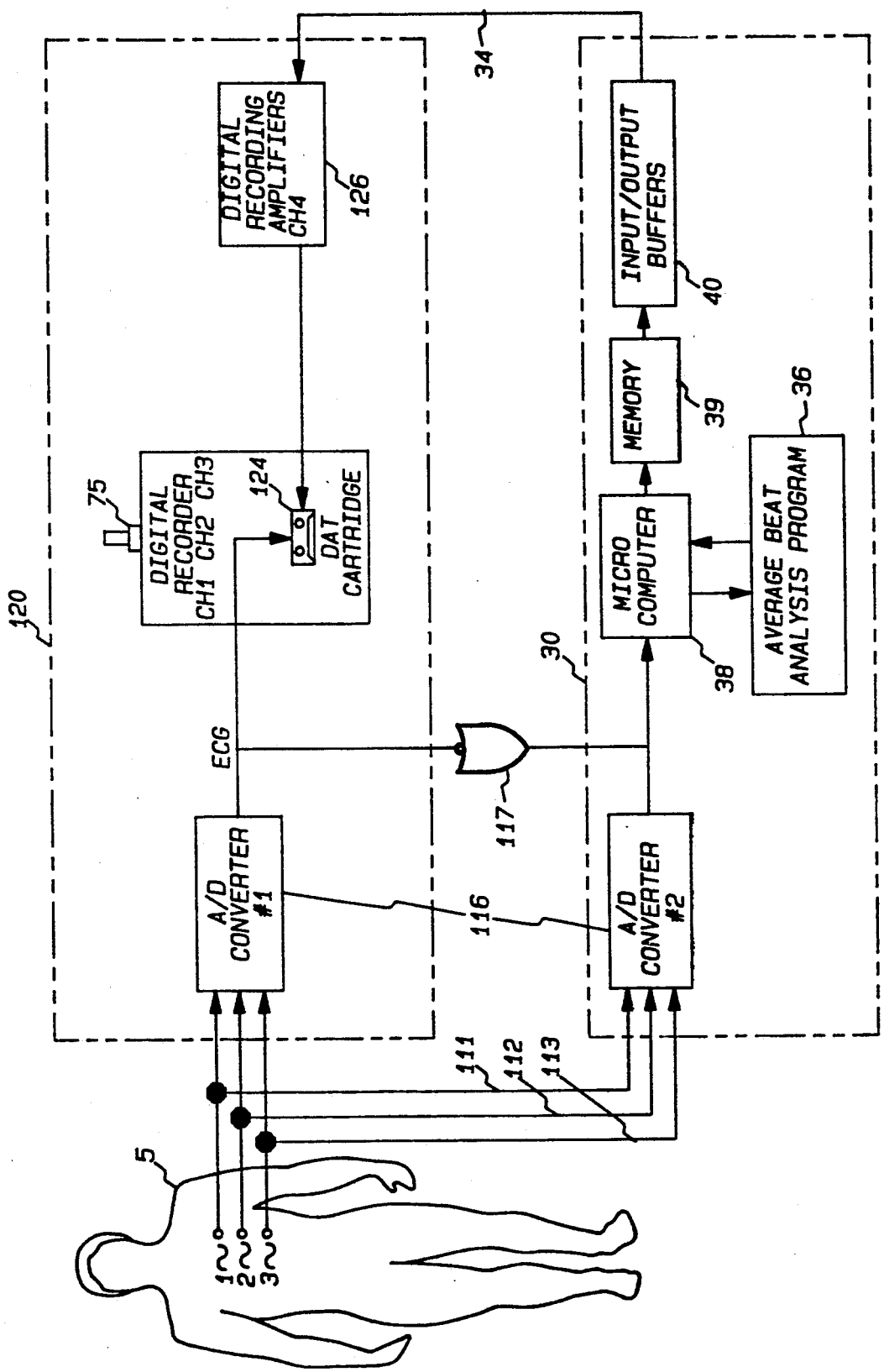
FIG. 5 is a block diagram representing Digital Audio Tape (DAT) tape being used as the storage medium for the recording portion of the present invention.

Referring to FIG. 5 which shows a second embodiment of the invention, wherein digital ambulatory tape (DAT) is employed as the storage medium. The following description will proceed in a manner similar to the above discussion in which analog magnetic tape was used as a storage medium.

The patient 5 is connected to three channels of electrocardiographic (ECG) sensor electrodes 1, 2, 3 which detect the bioelectric signals of the human heart. The sensor electrodes 1, 2, 3 are physically connected to ECG channels 111, 112, 113 and electrically connected to high resolution analog to digital convertors 116. The analog to digital convertors 116 provide a 12 bit digital word to the storage unit 120 and the signal averaging unit 30 that is representative of the analog signals received from sensor electrodes 1, 2, 3. Depending on resolution requirements, either two separate analog to digital convertors may required for each process, seen in FIG. 3 as A/D Convertor #1 and A/D Convertor #2, or a single high resolution analog to digital convertor could be used, shown in FIG. 5 as the hard wire OR 117, the preferred embodiment uses a 12 bit high resolution A/D that has hardwire OR 117 and the detailed descriptions will proceed accordingly. The storage unit 120 is a modified Holter recorder having as a storage medium a DAT tape cassette 124 which will receive a digitized version of the signals transmitted by sensor electrodes 1, 2, 3, from the analog to digital convertors 116, and then record these signals on DAT tape 124 in a defined format. Additionally, the signal averaged beats for each time epoch are inserted into the defined digital format. Cardiac event data is also digitally encoded into the digital format when the patient activates the event button 75.

The modification of storage unit 120 compared to conventional DAT based Holter recorders, is the capability to receive and store averaged beats 35 that have been digitally signal averaged by the signal averaging unit 30. The digital recording amplifiers 126 operate to receive the micropotential analysis results via serial bit stream 34 from signal averaging unit 30. These results are then stored in digital form on DAT tape 124. The micropotential analysis results are multiplexed into the data stream with the event button data 75. Therefore, this process is similar to the manner in which the signal averaged results are stored as discussed previously using analog magnetic tape as a storage medium, the differences being that DAT tape has no specific channel designation during recording.

Still referring to FIG. 5, input signals are received and processed by the signal averaging unit 30 in a manner similar to that discussed above under the first embodiment. High resolution A/D 116 performs a 12 bit analog to digital conversion of the sensor electrode input 1, 2, 3 received by the three ECG channels 111, 112, 113 which is then be used by the microcomputer 38 as data for the beat averaging analysis 36 program. The average beat analysis program 36 will perform a simultaneous digital average of all the desired beats. In the preferred embodiment 1000 beats will be averaged. The averaged beats will then be correlated with a previously defined correlation coefficcient, typically 0.98, thus eliminating extraneous nonrepetitive noise components and other irregular ECG beats. By performing the beat averaging analysis with a 12 bit digital word, the averaged beat can be resolved to less than a microvolt with a signal to noise ratio of one. Once microcomputer 38 has performed beat averaging analysis 36 on the desired data, it will store the averaged beat data 17, 18, 19 into memory 39, where it will be held prior to being output by the I/O Section 40 to the storage unit 120. Data from the signal averaging unit 30 will be used by storage unit 120 to store data in a defined format on a single multiplexed digital track.

Figure 6:
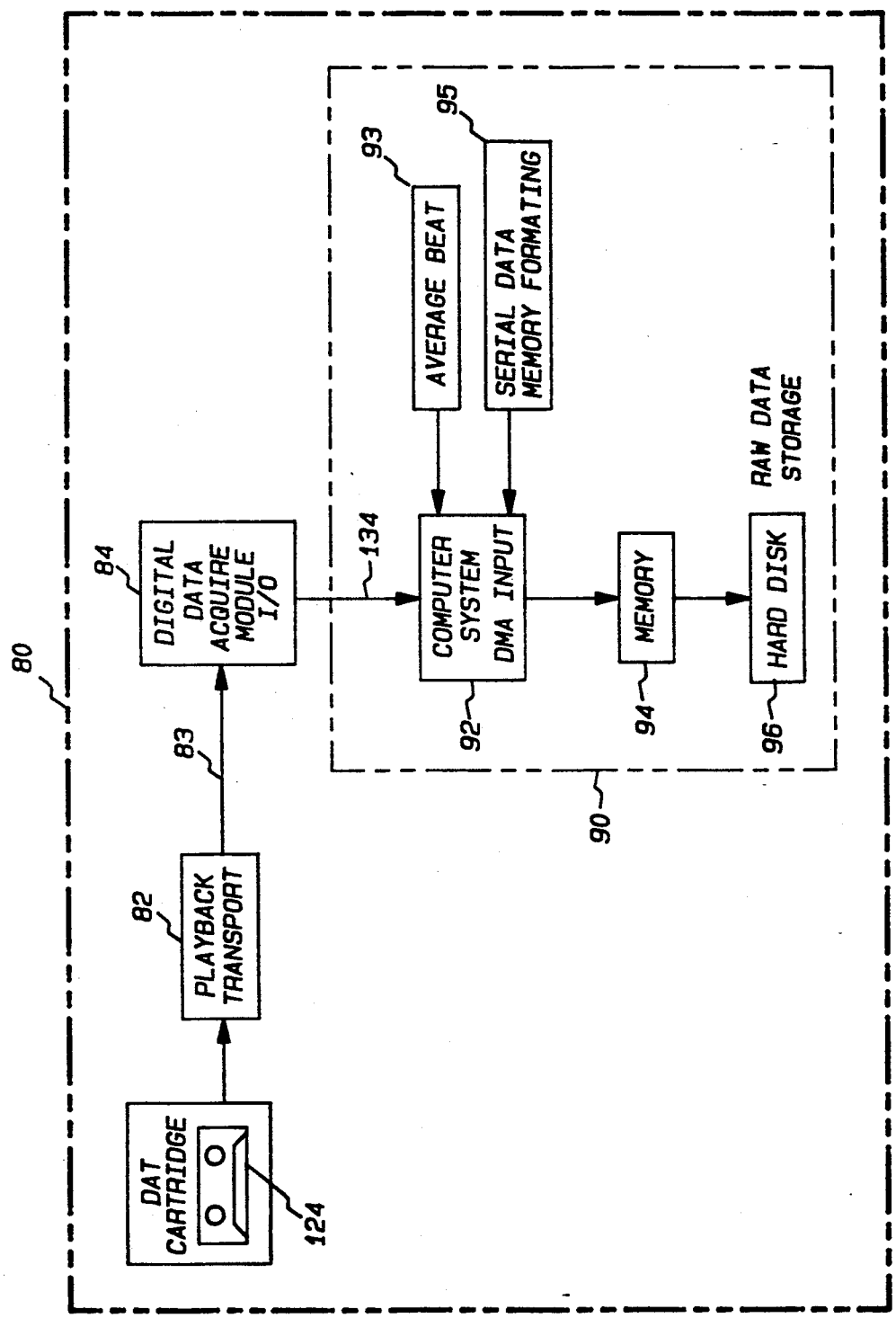
FIG. 6 is a block diagram of the playback system for the DAT based recording system as shown in FIG. 3.

Referring now to FIG. 6 which is the playback system for DAT recordings, generally referred to as 80, the system is a simplified version of the playback system discussed for the first embodiment of the invention due to the fact that the data recorded on the DAT tape is already in digital form and there is no need to have the digital encoding capabilities of the previous embodiment. DAT cartridge 124 having previously recorded data is placed in playback transport 82. Serial data 83 will be sent to acquire module 84 when DAT cartridge 124 is played back. Serial multiplexed data 134 is then sent from the acquire module 84 to computer system 90 containing three channels of ECG data directly multiplexed with the average beat digital data, patient event other data such as date, time of day and patient I/O.

Acquire module 84 in the DAT based embodiment is greatly simplified over the previous magnetic tape embodiment in not requiring tape motors or servo mechanisms as well as not requiring digital encoding. Acquired data 85 is sent from acquire module 84 to computer system 90 containing a computer with direct memory access (DMA) 92 functions performing average beat analysis 93 and serial data memory formatting 95. The serial data input is formatted to be placed into the computer memory 94 and hard disk 96 by the memory formatting program 95 so that high speed access of all digital data is possible during analysis. Analysis of the stored raw data is performed in a secondary operation by the analysis program using already established techniques.

Figure 7:
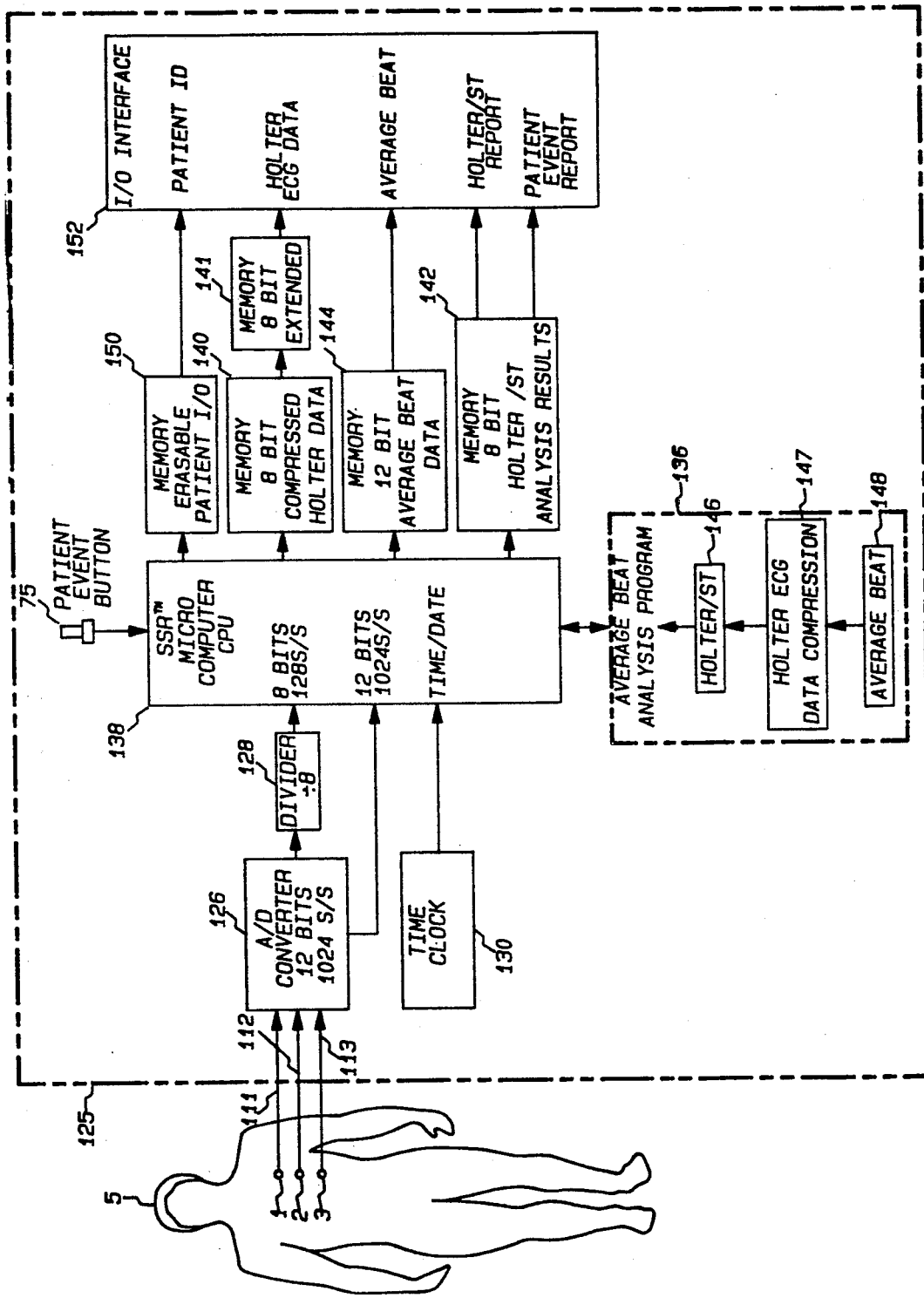
FIG. 7 is a block diagram for the recording portion of the present invention employing a Solid State storage device.

Referring to FIG. 7 a block diagram of the recording portion for the third embodiment of the invention is displayed employing a Solid State Recording SSR TM system (generally referred to as 125) device. Here the subject patient 5 can be seen wearing ECG electrodes 1, 2, 3, which are in turn connected to 12 bit analog to digital (A/D) convertor 126 via ECG channels 111, 112, 113. The bioelectric signals detected by electrodes 1, 2, 3 are converted into digital signals by A/D convertors 126 to be used by the SSR TM 125. The SSR TM microcomputer 138 will receive the digital data from divider 128 which converts the initial sample rate from 1024 s/s to 128 s/s. The four most significant bits are also eliminated to reduce the memory required to save the Holter EEG data to a more practical level. Compression algorithm 147 uses conventional techniques to reduce the amount of memory required to store Holter data into memory 140. In systems having extended memory 141 suitable for storing long term recordings of Holter data, such as periods of 24 hours or more, data compression is not required.

The SSR TM microcomputer 138 will also receive 12 bits of high resolution data from the A/D convertors 126 that is used by the SSR TM microcomputer 138 to perform signal averaging of digitally converted ECG data. Average beat analysis program 136 performs signal averaging on all segment beats (typically 1000) with a digital accuracy of 12 bits enabling the averaged beats to be resolved down to one microvolt or less at a signal to noise ratio of one. The average beat analysis program 136 correlates each beat to every other beat with an accuracy that is typically specified as 0.98. This procedure uses existing techniques which eliminates extraneous noise and other ventricular type beats prior to the final determination of the average. Apart from the similarities to the above discussed embodiments, the SSR TM microcomputer system 138 executes an ECG Compression Program 147 on the digitized Holter ECG data, to compress these digital signals simultaneously with average beat 148 performing signal analysis functions. By compacting the ECG data into a smaller memory, systems having relatively small amounts of memory can still perform real time analysis of micropotentials on an ambulatory basis, while storing a full record of multiple channel Holter ECG data.

Still referring to FIG. 7, the SSR TM system 125 stores the results of its computations in various memory areas. The Holter/ST results memory 142 stores the results of the Holter/ST analysis program 146 in 8-bit memory. Average beat 148 calculations are stored in Memory Averaged Beat Data 144 which is a 12 bit memory reflecting the high resolution used in the beat averaging process. The entire ECG Holter recording is stored in Holter Data Memory 140. Patient data, in the preferred embodiment, is stored in Erasable Patient I/O 150 which is essentially an $E^2PROM$ type memory which being a nonvolatile memory will retain the patient data during power down times while still being alterable. The I/O Interface 152 connects the SSR TM to a standard computer system for transfer of the stored results and for further processing and for further processing and plotting of the average beat data.

Figure 8:
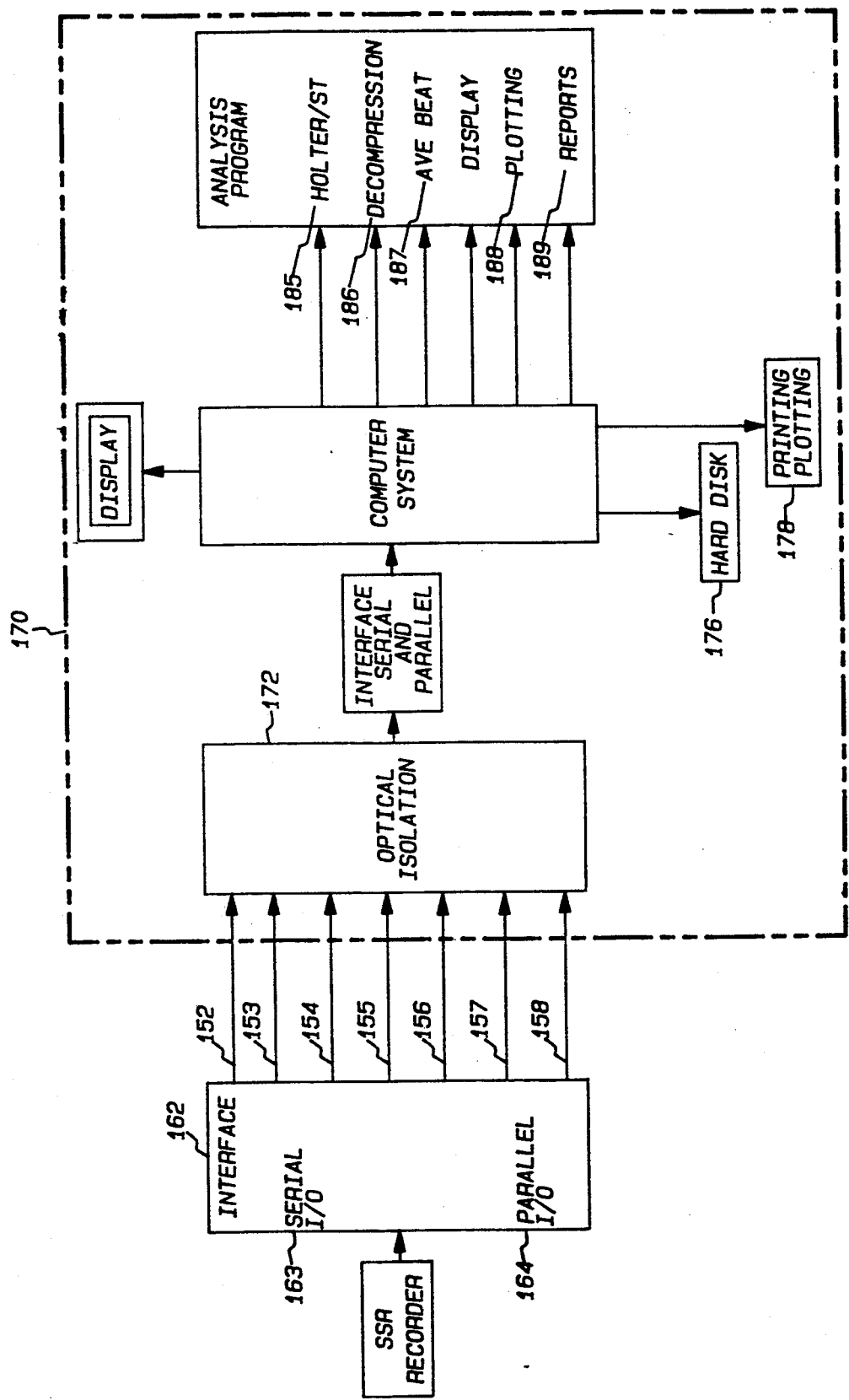
FIG. 8 is a block diagram for the playback system as envisioned in the embodiment of the present invention employing Solid State memory as a storage medium.

Referring now to FIG. 8, a block diagram showing the SSR TM playback system 160 for the SSR TM based version of the invention, interface 162 provides both serial I/O 163 and parallel I/O 164 will transmit the data to the analysis system 170. Data transferred across the interface 162 will include patient data 152, ECG data 153, interface control signals 154, averaged beat data 155, Holter/ST data 156, event data 158 and timing data 157. The recorder previously described in FIG. 8 outputs these signals in a conventional manner to the computer analysis system 170 via serial 163 and parallel 164 ports. Optical isolation 172 is a conventional device that is provided in the interests of patient safety. Data is downloaded from memory 174 and placed into hard disk 176 for storage. Separate analysis programs 180 are provided for each of the above stated types of data, these programs will perform analysis functions on each specific type of data. Holter/ST 185 is a program, typically known in the art, that analyzes data that has been received from compressed memory using standard decompression 186 program 186 to reverse the compression process employed by recorder 125 and places the data into a format suitable for analysis. However, as stated above in systems employing extended memory, the compression-decompression process is unnecessary. The digital average beat for the multiple channels is transferred as a block of data as defined for the recorder in FIG. 8. The availability of data relating to average beats 32 for a given time epoch of 10–15 minutes is already available from the recorder, thus, further processing by average beat 187 only consists of filtering and display plotting 188 as previously defined in U.S. Pat. No. 4,883,065 issued to Kelen which has been assigned to the assignee of the present invention. Additionally, analysis and plotting of this data can be performed in the frequency domain as further defined in U.S. patent application 07/658,505 (a continuation of U.S. patent application 07/496,976, both by Kelen and Henkin, and both also assigned to the assignee of the present invention) which matured into U.S. Pat. No. 5,109,862.

Figure 9:
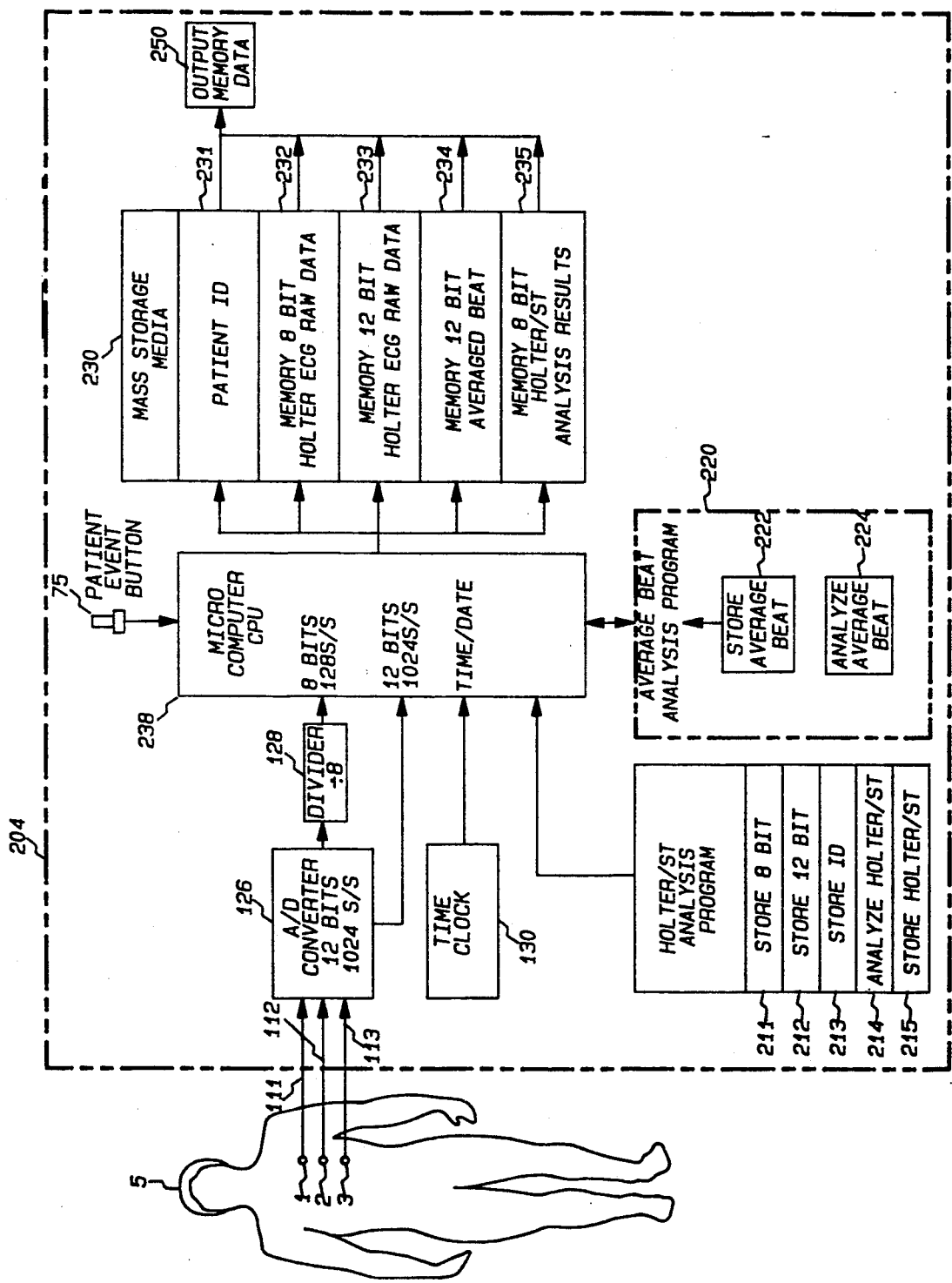
FIG. 9 is a block diagram for the recording portion of the present invention employing a mass storage device to store all raw and analyzed ECG data.

Referring to FIG. 9, a block diagram of the recording portion for the embodiment of the present invention employing a mass storage device 230 in place of the tape or solid state memory discussed in the previous embodiments. The embodiment using mass storage device 230 has similarities to the Solid State Recording system intended to be sold under the trademark "SSR" TM system discussed above. The most basic difference int he present embodiment being that mass storage device 230 is used to store the recorded/analyzed data. Proceeding in a manner similar to the discussion under the "SSR" TM embodiment, patient 5 wears electrodes 1, 2, 3, which are electrically connected to 12 bit analog to digital (A/D) convertor 126 via ECG channels 111, 112, 113. Bioelectric signals detected by electrodes 1, 2, 3 are converted into digital signals by A/D convertors 126 to be used by the system microcomputer 138. This embodiment differs from the previous embodiments by employing mass storage device 230 to store the recorded and analyzed data. Mass storage device 230 provides a mass storage capability not available with the solid state storage of the previous embodiment. Any of a variety of devices currently available can be used as mass storage device 230. Among the possible technologies that can function as mass storage device 230 are storage devices made from magnetic disc, optical disc or magneto-optical, as well as memory card technology which can be either solid state or optical. Mass storage device 230 also provides the random access capability not available with tape storage discussed in previous embodiments. Any of the aforementioned technologies can be used as mass storage device 230.

In order to storage all the recorded and analyzed data, various fields are created within mass storage device 230 for the different types of data. These fields include patient ID 231, Raw 8-Bit Data 232, Raw 12-Bit Data 233, Averaged 12-Bit data 234, and Holter/ST Analysis results 235.

Microcomputer 138 receives digital data from divider 128 and performs functions contained in Holter analysis program 210 and average beat analysis program 220. Here, Holter/St Analysis 210 contains the functions: store 8-bit 211 to store raw 8-bit data in its respective field; store 12-bit 212 to storage 12-bit raw data in its respective field; store ID 213 to store patient ID in its respective field; analyze Holter/ST 214 to initiate CPU 138 computations relating to the analysis of the ST segment of electrocardiographic recordings; store Holter/ST 215 to store the results of the Holter/ST segment analysis; and store averaged data 216 to store the data that results from the averaging of. This parallels the functions of the Holter/ST Analysis Program of the solid state embodiment discussed previously. However, the mass storage device 230 embodiment requires functions to be specifically designed interface with the specific type of media used as mass storage device 230. The Average Beat Analysis Program 220, contains the function store average beat 222 and analyze average beat 224 which correlate to the average beat 148 function previously described. Functions related to data compression as detailed under the solid state embodiment discussed previously are not required using mass storage device 230 due to the large storage capacity. Furthermore, compression techniques tend to loose or distort data and are, therefore, undesirable.

The "SSR~ TM microcomputer 138 will receive data in much the same way as did the previous embodiment, here, 12 bits of high resolution data from the A/D convertors 126 that is used by the "SSR" TM microcomputer 138 to perform signal averaging of digitally converted ECG data. Average beat analysis program 136 performs signal averaging on all segment beats (typically 1000) with a digital accuracy of 12 bits enabling the averaged beats to be resolved down to one microvolt or less at a signal to noise ratio of one. The average beat analysis program 136 correlates each beat to every other beat as discussed previously, using existing techniques which eliminates extraneous noise and ventricular type beats prior to the final determination of the average.

Figure 10:
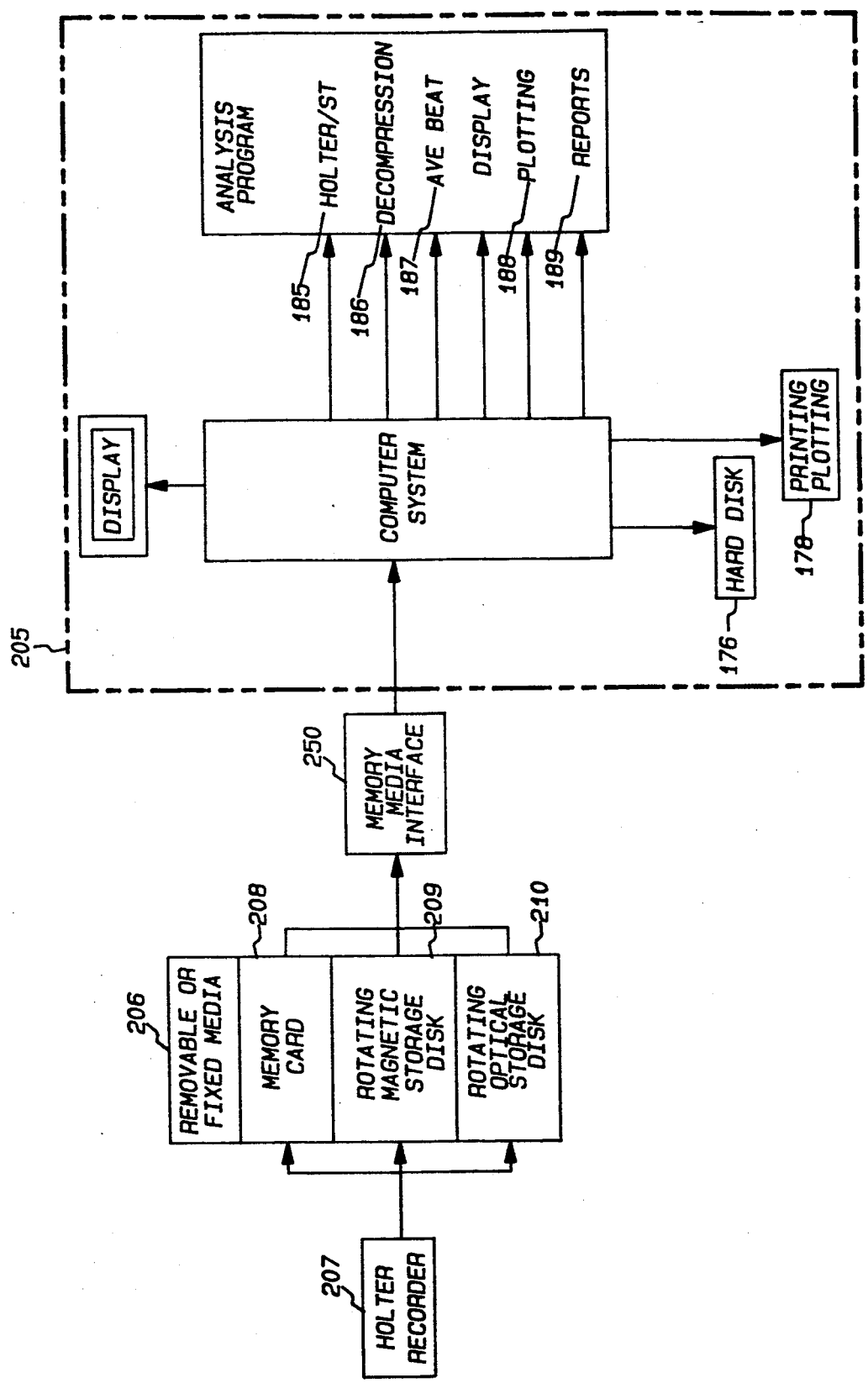
FIG. 10 is a block diagram for the playback system as envisioned in the mass storage device based embodiment of FIG. 9.

Referring now to FIG. 10, a block diagram showing the playback system 205 envisioned for the recording-/analysis system of FIG. 9, memory media interface 250 provides the data to the analysis system 205. Data transferred across memory media interface 250 will include patient ID data 231, 8-bit ECG data 232, 12-bit ECG data 233, 12-bit averaged beat data 234, Holter/ST analysis results 235 and event data 236. The recorder previously described in FIG. 9 outputs these signals in a conventional manner to the computer analysis system 205 via memory media interface 250. Data is taken from rotatable disc storage means 230 and placed into hard disk 176 for storage. Separate analysis programs 180 are provided for each of the above stated types of data, these programs will perform analysis functions on each specific type of data. Holter/ST 185 is a program, typically known in the art, that analyzes data that has been received from compressed memory using standard decompression 186 program 186 to reverse the compression process employed by recorder 125 and places the data into a format suitable for analysis.

The digital average beat for the multiple channels is transferred as a block of data as defined for the recorder in FIG. 9. The availability of data relating to average beats 32 for a given time epoch of 10–15 minutes is already available from the recorder, thus, further processing by average beat 187 only consists of filtering and display plotting 188.

The invention as disclosed hereinabove describes embodiments of the invention as it may be practiced using presently available commercial recording mediums. However, the invention as disclosed herein may also be practiced using recording devices and mediums that are presently being developed and are not as yet widely commercially available. Devices such as the new digital cassette presently being developed will be in direct competition with DAT digital cartridge, and could also be used to practice the present invention. New recordable optical disks devices have been introduced which can hold large amounts of digital data could also be used to practice the invention disclosed herein. Many other recording devices and/or mediums that are presently emerging or will emerge in the future could also be used to practice the invention.

The preferred embodiments of the invention have disclosed the best modes presently known to the inventor, however, it should be understood that various modifications to the embodiments disclosed herein, will be obvious to persons skilled in the referenced arts, and that such modifications are still within the spirit and scope of the invention.

What is claimed is:

1. A long term ambulatory (Holter) based electrocardiographic (ECG) system for recording and analyzing bioelectric signals of the human heart comprising:
    electrode means, consisting of a plurality of electrocardiographic (ECG) electrodes adapted for placement on a human patient, for detecting bioelectric signals of the human heart and generating, therefrom, an analog signal;
    recorder means electrically connected to said plurality of electrodes for making a real time recording of bioelectric signals detected by said electrodes, said recorder means having a plurality of data channels such that there is at least one data channel for each of said ECG electrodes;
    storage means contained within said recorder means;
    digitizing means contained within said recorder for converting said analog signals into a series of digital signals representative of bioelectric signals of the human heat;
    analysis means contained within said recorder means for taking a sample form said series of digital signals and computing, therefrom, a signal average for each of said ECG data channels.

2. The invention of claim 1 wherein at least one of said data channels is used to record said summations of said signal averages for each channel.

3. The invention of 1, wherein said analysis means includes acquisition means to acquire said sample from a predetermined time period.

4. The invention of claim 3, wherein said acquisition means acquires said sample in response to patient activation.

5. The invention of claim 1 wherein said digitizing means contains high resolution means for performing high resolution sampling and digitizing.

6. The invention of claim 1 wherein said storage means is selected from the group consisting of: (1) analog magnetic tape; (2) digital audio tape (DAT); (3) solid state recording (SSR) with limited memory; (4) solid state memory recording with extended memory; (5) rotating magnetic media; (6) rotating optical media; (7) rotating magneto-optical media; and (8) removable memory card media.

7. The invention of claim 1 wherein said analysis means further comprises a microprocessor having available memory means to store instructions for said microprocessor, said microprocessor executing instructions with said memory means to perform said sampling and signal averaging under control of a microcode program embedded in a nonvolatile memory source as well as placing said summated signal averaged signals in a RAM source prior said placing onto said storage means.

8. The invention of claim 1 further including an ECG analysis computer having playback means for playing back all recorded ECG signals and summated signal averaged signals to said ECG analysis computer, said playback means having high speed means to play back recordings at a speed many times the real time recording speed.

9. The invention of claim 8 further including means for storing all recorded signals in a digital format in a storage area, said storage consisting of an area of memory or a disk storage device.

10. The invention of claim 1 wherein said analysis means further includes means to correlate coefficient to provide a basis for eliminating nonrepetitive noise and irregular beats.

11. A method of recording electrocardiographic data to provide the capability for the analysis of the presence of micropotentials comprising the steps of:
    attaching a plurality of electrocardiographic (ECG) electrodes to a subject patient, each of said electrodes detecting a bioelectric signal of the human heart and generating, therefrom, an analog ECG signal;
    converting each of said analog ECG signals into a digital representation of said analog ECG signal such that each of said digital representations represents a specific point in time relative to said analog ECG signal;
    recording said bioelectric signals of the human heart on a plurality of data channels such that each of said bioelectric signals is separately stored on one of said plurality of data channels;
    sampling and signal averaging of said digital representations for each of said analog ECG signals represented by said digital representations;
    summating said averaged digital representations;
    storing said summated signal averaged version of said digital representations on at least one of said channels.

12. The method disclosed in claim 11 wherein the step of recording of said bioelectric signals of the human heart consists of long term ambulatory recording of said analog ECG signals generated by said plurality of electrodes.

13. The method disclosed in claim 11 wherein the step of recording said bioelectric signals of the human heart consists of recording said digital representations derived from said converting step.

14. The method disclosed in claim 11 wherein the step of sampling and signal averaging further includes:
    obtaining a correlation coefficient;
    correlating each beat to said correlation coefficient; and
    eliminating nonrepetitive noise and irregular beats based on results obtained from said correlating step.

15. The method of claim 11 wherein the step of recording further includes employing a storage device which is selected from the group consisting of (1) analog magnetic tape; (2) digital audio tape (DAT); (3) solid state recorder with limited memory; (4) solid state recorder with extended memory; (5) rotating magnetic media; (6) rotating optical media; (7) rotating magneto-optical media; and (8) removable memory card media.

16. The method of claim 11 further including performing the step of sampling and signal averaging during a predetermined time period.

17. The method as disclosed by claim 11 wherein the step of storing further includes interrupting the recording of at least one of said plurality of data channels used to record said ECG signals and placing on said interrupted channel said summated signal averaged signals.

18. The method disclosed by claim 11 further comprising the step of playing back all said ECG data and all said summated signal averaged signals, at a speed many times that used in said recording step to record said ECG data and said summated signal averaged signals, to an ECG analysis system.

19. A system for detecting and analyzing electrocardiographic micropotentials of the human heart comprising:
- a Holter recorder being electrically connected to a plurality of electrodes, said recorder having a plurality of data channels such that there is at least one data channel for each of said plurality of electrodes, said recorder being capable of sensing and recording the bio-electric signals or the human heart;
- analysis means contained within said recorder, said analysis means being operative to create a digital signal average for each of the signals received from said electrodes by said recorder;
- storage means to record said digital signal averages on said recorder.

20. The invention of claim 19 wherein said analysis means is capable for high resolutions digitization of signals received via said electrodes.

21. The invention of claim 19 wherein said signal average, produced by said analysis means, is a simultaneous digital average of a predetermined sample of signals received via said electrodes.

22. The invention of claim 19 wherein said storage means records said signal average by interrupting one of said channels used to record data for one of said electrodes and placing thereon, said digital signal average.

23. The invention of claim 19 wherein said storage means records said signal average on a separate channel from tracks used to record electrode data.

24. The invention of claim 23 wherein said separate track is a timing track used to store a timing signal that is operative in synchronizing ECG data received from said electrodes, said timing signal being modulated with said signal averaged beat data, thereby, storing said signal averaged beat data on said timing track.

25. The invention of claim 19 further comprising playback means to reproduce recorded digital signal averages.

26. The invention of claim 19 wherein said analysis means further includes means to correlate each beat to a previously defined correlation coefficient thus providing a basis of eliminating extraneous nonrepetitive noise and other irregular beats.

27. The invention of claim 19 wherein said storage means is selected from the group consisting of: (1) analog magnetic tape; (2) digital audio tape (DAT); (3) solid state recorder with limited memory; (4) solid state recorder with extended memory; (5) rotating magnetic media; (6) rotating optical media; (7) rotating magneto-optical media; and (8) removable memory card media.

* * * * *